(12) United States Patent
Amirav (10) Patent No.: US 7,247,495 B2
(45) Date of Patent: Jul. 24, 2007

(54) MASS SPECTROMETER METHOD AND APPARATUS FOR ANALYZING A SAMPLE IN A SOLUTION

(76) Inventor: Aviv Amirav, 5 Hayaar Alley, Hod Haaharon 45269 (IL)

( * ) Notice: Subject to any disclaimer, the term of this patent is extended or adjusted under 35 U.S.C. 154(b) by 441 days.

(21) Appl. No.: 10/219,367

(22) Filed: Aug. 15, 2002

(65) Prior Publication Data

US 2003/0003595 A1    Jan. 2, 2003

Related U.S. Application Data

(63) Continuation-in-part of application No. 09/437,951, filed on Nov. 10, 1999, now abandoned.

(30) Foreign Application Priority Data

Nov. 23, 1998 (IL) .................................. 127217

(51) Int. Cl.
G01N 30/72 (2006.01)
G01N 1/22 (2006.01)
H01J 49/02 (2006.01)
H01J 49/10 (2006.01)
H01J 49/26 (2006.01)
B01D 59/44 (2006.01)

(52) U.S. Cl. .................... 436/173; 250/281; 250/282; 250/288; 436/181

(58) Field of Classification Search ........ 250/281–282, 250/288; 436/173, 181
See application file for complete search history.

(56) References Cited

U.S. PATENT DOCUMENTS

| | | | | |
|---|---|---|---|---|
| 4,214,160 A | * | 7/1980 | Fies et al. ................... | 250/292 |
| 4,388,531 A | * | 6/1983 | Stafford et al. ............. | 250/427 |
| 4,542,293 A | * | 9/1985 | Fenn et al. .................. | 250/288 |
| 4,861,989 A | * | 8/1989 | Vestal et al. ................ | 250/288 |
| 4,863,491 A | * | 9/1989 | Brandt et al. ................... | 95/29 |
| 4,952,802 A | * | 8/1990 | Duryea ....................... | 250/288 |
| 4,968,885 A | * | 11/1990 | Willoughby ................ | 250/288 |
| 4,977,785 A | * | 12/1990 | Willoughby et al. ..... | 73/863.12 |

(Continued)

OTHER PUBLICATIONS

Brink, G. O. Review of Scientific Instruments 1966, 37, 857-860.*

(Continued)

Primary Examiner—Arlen Soderquist
(74) Attorney, Agent, or Firm—J. Harold Nissen; Lackenbach Siegel (57) ABSTRACT

The invention provides a mass spectrometric method for analyzing a sample in a solution, including the steps of directing a flow of a solution containing sample compounds to be analyzed towards a supersonic nozzle having an input end and an output end; vaporizing the solution and sample prior to its expansion from the output end of said supersonic nozzle; allowing expansion of the vaporized sample and solution from said supersonic nozzle into a vacuum system, forming a supersonic molecular beam with vibrationally cold sample molecules; ionizing the vaporized sample compounds with electrons while contained as vibrationally cold molecules in said supersonic molecular beam; mass analyzing the ions formed from said sample compounds; detecting said ions formed from said sample compounds after mass analysis, and processing the data obtained from the resulting mass spectral information, for identifying and/or quantifying the chemical content of said sample. The invention also provides apparatus for analyzing a sample in a solution.

24 Claims, 6 Drawing Sheets

U.S. PATENT DOCUMENTS

| | | | | |
|---|---|---|---|---|
| 5,055,677 A | * | 10/1991 | Amirav et al. | 250/282 |
| 5,162,650 A | * | 11/1992 | Bier | 250/288 |
| 5,526,682 A | * | 6/1996 | Jarrell et al. | 73/61.55 |
| 5,742,050 A | * | 4/1998 | Amirav et al. | 250/288 |
| 6,525,314 B1 | * | 2/2003 | Jarrell et al. | 250/297 |

OTHER PUBLICATIONS

Randall, L. G. et al, Review of Scientific Instruments 1981, 52, 1283-1295.*
Roth, P. et al, Science Direct abstract of Journal of Aerosol Science 1994, 25, 61-73.*
Tinke, A. P. et al, Analytical Chemistry 1994, 66, 3005-3012.*
Dagan, S. et al, Journal of the American Society for Mass Spectrometry 1995, 6, 120-131.*
Kientz, C. E. et al, Analytical Chemistry 1996, 68, 675-681.*
Dagan, S. et al, Journal of the American Society for Mass Spectrometry 1996, 7, 550-558.*
Mayer, P. M. et al, International Journal of Mass Spectrometry and Ion Processes 1996, 156, 133-139.*
Smith, R. D. et al, Analytical Chemistry 1984, 56, 2971-2973.*
Nishi, N., Zeitschrift fuer Physik D: Atoms, Molecules and Clusters 1990, 15, 239-255.*
Riley, J. S. et al, International Journal of Mass Spectrometry and Ion Processes 1994, 131, 295-305.*
DeKieviet, M. et al, Review of Scientific Instruments 2000, 71, 2015-2018.*
Olesik, S. V. et al, International Journal of Mass Spectrometry and Ion Processes 1984, 57, 299-314.*
Rizzo, T. R. et al, Oxford Series on Optical Sciences 1990, 1, 402-422.*
Roth, P. et al, Journal of Aerosol Science 1994, 25, 61-73.*
Yamamoto, Y. et al, International Conference on Natural Gas Hydrates, 2nd, Toulouse,Jun. 2-6, 1996, 355-362, Publisher: PROGEP, Toulouse, France.*
Blakley, C. R. et al, Journal of Chromatography 1978, 158, 261-276.*
Randall, L. G. et al, Analytical Chemistry 1978, 50, 1703-1705.*
Blakley, C. R. et al, Analytical Chemistry 1980, 52, 1636-1641.*
Blakley, C. R. et al, Clinical Chemistry 1980, 26, 1467-1473.*
Milne, T. A. et al, Energy from Biomass and Wastes 1984, 8, 1371-1393.*
Jonkman, H. T. et al, Journal of Physical Chemistry 1985, 89, 4240-4243.*
Lee, E, D. et al, Analytical Chemistry 1987, 59, 1309-1312.*
Danon, A. et al, Review of Scientific Instruments 1987, 58, 1724-1726.*
Amirav, A. et al, International Journal of Mass Spectrometry and Ion Processes 1990, 97, 107-113.*
Amirav, A., Journal of Physical Chemistry 1990, 94), 5200-5202.*
Ligon, W. V., Jr. et al, Analytical Chemistry 1990, 62, 2573-2580.*
Jones, G. G. et al, Analytical Chemistry 1991, 63, 460-463.*
Tinke, A. P. et al, Journal of Chromatography 1991, 554, 119-124.*
Bier, M. E. et al. Journal of the American Society for Mass Spectrometry 1993, 4, 38-46.*
Cappiello, A. et al, Analytical Chemistry 1993, 65, 1281-1287.*
Huang, S. K. et al, Rapid Communications in Mass Spectrometry 1993, 7, 722-724.*
Jedrzejewski, P. T. et al, Journal of Chromatography A 1994, 677, 365-376.*
Kuhnke, K. et al, Review of Scientific Instruments 1994, 65, 3458-3465.*
Amirav, A. et al, Applications of Free-Jet, Molecular Beam, Mass Spectrometric Sampling, Proceedings, Estes Park, Colo., Oct. 11-14, 1994, 43-50, Editor(s): Milne, T., Publisher: National Renewable Energy Laboratory, Golden, Colo.*
Lawson, G. et al, Applied Organometallic Chemistry 1996, 10, 135-143.*
Dagan, S. et al, Journal of the American Society for Mass Spectrometry 1996, 7, 737-752.*
Slobodnik, J. et al, Journal of Chromatography A 1996, 730, 353-371.*
Malakhovskii, A. et al, Chemical Physics 1997, 221, 215-223.*
Manini, P. et al, Rapid Communications in Mass Spectrometry 1998, 12, 883-889.*
Thomson, B. A., Journal of the American Society for Mass Spectrometry 1998, 9, 187-193.*
Cappiello, A. et al, Journal of the American Society for Mass Spectrometry 1998, 9, 993-1001.*
Amirav, A. et al, Journal of the American Society for Mass Spectrometry 2000, 11, 587-591.*

* cited by examiner

MASS SPECTROMETER METHOD AND APPARATUS FOR ANALYZING A SAMPLE IN A SOLUTION

This application is a continuation-in-part of U.S. patent application Ser. No. 09/437,951 filed Nov. 10, 1999, and now abandoned.

FIELD OF THE INVENTION

The present invention relates to a mass spectrometer method and apparatus for analyzing a sample in a solution.

BACKGROUND OF THE INVENTION

Mass spectrometry (MS) is a central analytical technology that finds a large variety of applications in a broad range of fields, especially when coupled with a separation technique such as gas chromatography (GC) or liquid chromatography (LC). GC-MS has become the most widely used form of mass spectrometry.

GC-MS is generally characterized by very good sensitivity, excellent separation resolution, very good molecular identification capability through the rich ion fragmentation pattern and extensive libraries available for identification, relative ease of use and low cost. However, GC-MS suffers from a major limitation: its inability to analyze thermally labile (and relatively non-volatile) compounds that tend to dissociate in the GC injector, column or MS electron impact ion source. This drawback is especially severe when relatively large bio-molecules and drugs are encountered.

Thus, various methods of LC-MS were developed for the analysis of these compounds, and LC-MS is now experiencing rapid development and growth in its use and applications. The major problem in the coupling of an LC to the MS is in the need to avoid large solvent load on the MS high vacuum system, coupled with the need to preserve molecular integrity. Accordingly, the type of LC-MS is usually named after its MS interface and ionization technique. Today, the major LC-MS techniques are:

1. Particle Beam LC-MS (PB-LC-MS)

In this method, the LC effluent is sprayed through a thermally assisted or pneumatic nebulyzer into a drying desolvation chamber to form small droplets or particles that expand through a supersonic nozzle into a differentially pumped vacuum chamber before entering the MS ion source. The heavy sample particles (hence the name particle beam) formed after solvent vaporization move preferentially forward, while the solvent molecules are pumped away. Sample/solvent separation factor of over $10^5$ can be achieved. The sample particles are thermally vaporized inside the electron ionization (EI) ion source, and the sample compounds are ionized as gas phase molecules in thermal equilibrium with the heated ion source walls. The EI ion source is a standard ion source with an added heated plate to assist with the intra ion source thermal vaporization of the particles. PB-LC-MS is a useful technique especially due to its EI mass spectra, which provide library-searchable EI mass spectra for easy molecular identification. However, PB-LC-MS is limited in its ability to analyze very thermally labile compounds, due to the intra-ion source thermal vaporization stage. Furthermore, compounds with low volatility tend to exhibit ion source-related peak tailing, due to lengthy intra-ion source adsorption-desorption cycles. This peak tailing can be reduced by further heating the ion source, but with the major penalty of excessive molecular and/or molecular ion dissociation. PB-LC-MS also suffers from non linear signal dependence on the sample concentration (and matrix) due to variation in the particle transmission versus its size due to partial vaporization of small sample compounds that are pumped away and lost with the solvent.

2. Atmospheric Pressure Chemical Ionization (APCI)

In APCI, the LC effluent is sprayed and ionized in a zone of corona discharge, at about 1 atmosphere. The solvent molecules and other gases are ionized and then the vaporized sample compounds are ionized through a series of atmospheric pressure charge transfer and chemical ionization processes. The sample ionization efficiency is very high, but typically only $10^{-4}$ of the ions are transferred to the MS through a 100μ nozzle or ion transfer tube. In contrast to the particle beam method, APCI involves with high-pressure sample vaporization. APCI is a soft ionization technique that finds growing use. However, the existence of mostly $M^+$ ions is a limitation that is usually overcome by the use of costly and complex MS-MS instrumentation that enables molecular ion dissociation and provides fragment information. In addition, APCI is relatively ineffective for the ionization of non-polar compounds; its ionization efficiency is compound-dependent and therefore non-quantitative, and thus requires compound-specific calibration for quantification.

3. Electrospray LC-MS (ES-LC-MS)

ES-LC-MS has recently become the most popular LC-MS method. It is based on spray formation from a highly charged needle and spontaneous ion evaporation from the highly charged droplets. The main attribute of electrospray (ES) is the possible formation of multi-charged molecular ions that enable very high mass determination up to about $10^5$ Dalton. It is also currently the most sensitive LC-MS method. ES can also be used with small molecules, but it suffers from a non-uniform response (non-quantitative detection) that may vary substantially among different compounds and has to be optimized for each molecule separately. In general, ES sensitivity is reduced for both small molecules and non-polar compounds. MS-MS instrumentation is also desired with ES, in order to provide fragment information and to enable better identification capability in view of the lack of ES mass spectral libraries. Adduct ion formation and complex matrix effects also hamper the effectiveness of both APCI and ES.

The use of supersonic molecular beams (SMB) for sampling and ionization in mass spectrometry was explored, aimed at improving all aspects of GC-MS with special emphasis on the development of improved, fast GC-MS. Supersonic molecular beams are characterized by the following features, which are of importance to mass spectrometry:

Extreme Intra-molecular Vibrational-rotational Supercooling:

Upon the expansion of organic compounds from a supersonic nozzle into a vacuum system, significant vibrational and rotational supercooling occurs. Thus, upon collimation a supersonic molecular beam is formed with vibrationally cold sample molecules for its further ionization by electrons or on a surface.

This intra-molecular cooling considerably improves the level of mass spectral information provided by electron ionization, when the sample compounds are ionized as vibrationally cold molecules contained in the supersonic molecular beam. The molecular ion abundance is largely enhanced and it is practically always exhibited, combined with the library-searchable fragment ions. Peak tailing due to lengthy intra ion source adsorption-desorption cycles is eliminated and matrix interference is reduced at the molecular and high mass fragment ions. Isomer and other structural effects are amplified and isotope abundance and elemental information is enabled. This enhanced information is provided even for thermally labile and relatively non-volatile compounds.

Unidirectional Motion with Controlled Hyperthermal Kinetic Energy up to 30 eV:

This directional kinetic energy enables a very effective ionization method called Hyperthermal Surface Ionization (HSI). HSI is based on the hyperthermal surface scattering of the sample compound from a suitable surface such as rhenium oxide, having a high surface work function. In HSI, the molecular kinetic energy is used to effectively bridge upon the surface ionization potential (IP-φ). Thus, the hyperthermal surface scattering is followed by spontaneous molecular ionization that can be very effective for compounds with relatively low molecular ionization potentials, such as polycyclic aromatic hydrocarbons (PAHs) or drugs. HSI is also a selective ionization method that is thus effective for the detection of drugs and PAHs in complex matrices, due to the reduced efficiency of aliphatic compounds ionization. HSI is potentially the most efficient mass spectrometric ionization due to very high ionization yield (up to 10%), its unique fragmentation pattern which can exhibit a single molecular or fragmented ion and the reduced vacuum background of the thermal molecules.

High Flow Rate (100-500 ml/min) Atmospheric Pressure Sample Inlet Capability, Combined with Heavy Species Focusing in the Beam Axis (Jet Separation):

This feature simplifies the transfer of the sample compounds from a GC or LC, according to the present invention.

HSI is potentially the most efficient mass spectrometric ionization method, due to its very high ionization yield (up to 10%), its unique fragmentation pattern which can exhibit a single molecular or fragmented ion, and the reduced vacuum background of the thermal molecules.

Up to now, the technique of mass spectrometry with supersonic molecular beams (SMB-MS) was successfully employed with gas phase samples, provided either from a direct sample introduction device after thermal vaporization, or from a gas chromatograph. However, its coupling with liquid samples of thermally labile compounds or with the output of an LC was not performed, despite the considerable merits of LC-MS, due to several major problems that must be considered and overcome:

a) The problem of intact vaporization of thermally labile compounds is central to the achievement of this goal. This is a major and complex problem that cannot be overcome by any standard, known approach.
b) Isolated vaporized sample compounds must be vibrationally cooled, avoid shock wave heating, collimated, properly enriched in the SMB, and be ionized while contained in the SMB for the preservation of the merits of SMB.
c) The liquid solvent load on the vacuum pumps needs to be considered, including its effect on the molecular cooling, aerodynamic acceleration and jet separation efficiency.
d) Peak tailing from all sources must be eliminated, combined with molecular cooling in the supersonic beam.
e) Cluster and adduct ion formation must be avoided or minimized.
f) All of the above items must be achieved with high sample transfer and ionization efficiency.

SUMMARY OF THE INVENTION

In accordance with the present invention, there is therefore provided a mass spectrometric method for analyzing a sample in a solution, comprising the steps of directing a flow of a solution containing sample compounds to be analyzed towards a supersonic nozzle having an input end and an output end; vaporizing the solution and sample prior to its expansion from the output end of said supersonic nozzle; allowing expansion of the vaporized sample and solution from said supersonic nozzle into a vacuum system, forming a supersonic molecular beam with vibrationally cold sample molecules; ionizing the vaporized sample compounds with electrons while contained as vibrationally cold molecules in said supersonic molecular beam; mass analyzing the ions formed from said sample compounds; detecting said ions formed from said sample compounds after mass analysis, and processing the data obtained from the resulting mass spectral information, for identifying and/or quantifying the chemical content of said sample.

The invention further provides a mass spectrometer apparatus for analyzing a sample in a solution, comprising means for directing a flow of a solution containing sample compounds to be analyzed towards a supersonic nozzle having an input end and an output end; means for vaporizing said solution and sample prior to their expansion from the output end of said supersonic nozzle; said supersonic nozzle enabling expansion of said vaporized sample into a vacuum system, forming a supersonic molecular beam which contains vaporized solution and vibrationally cold sample molecules; Electron ionization ion source means for ionizing said vaporized sample compounds while contained as vibrationally cold molecules in said supersonic molecular beam; mass analyzer means for the mass analysis of the ions formed from said sample compounds; an ion detector for detecting said ions formed from said sample compounds after mass analysis, and means for data processing of the mass spectral information obtained, for identifying and/or quantifying the chemical content of said sample.

The novel approach of the present invention, using liquid sample mass spectrometry with SMB, possesses several distinct and important advantages over the prior art:

1) A library mass spectral search is enabled, unlike with APCI and ES. This is a very important advantageous feature, as it enables fast and reliable molecular identification that is also considered to be legally defensible. Library identification of EI mass spectra can also be automated with the aid of appropriate software.
2) Extended mass spectral information is provided, which is superior to that provided by PB-MS or by any other liquid sampling MS method. In electron ionization of vibrationally cold molecules in the SMB, the relative mass spectral abundance of the molecular (and sometimes high mass fragments) ion is enhanced and it is practically always observed and thus can be trusted. The molecular ion is the single most important mass spectral information, without which, standard library identification cannot be fully trusted in view of homologous and other similar compound mass spectra. Furthermore, mass spectra of vibrationally cold molecules exhibits significantly amplified isomer mass spectral effects that enable improved isomer identification. The molecular ion and other high mass fragments are known to contain detailed structural information unavailable in any other ionization method, which is significantly amplified in EI of SMB cold molecules. In addition, the availability of the molecular ion without interference from self chemical ionization exposes the genuine isotope abundance in the group of isotopers mass spectral peaks near the molecular ion. This isotope information is important by itself and can further be used for translation into empirical formulas assuming known isotope abundances, which otherwise can be obtained only with expensive high-resolution mass analyzers. It is further noted that due to the vibrational cooling, the electron energy is the single parameter that controls the degree of molecular ion fragmentation and thus, low electron energy EI can serve as a soft ionization method with limited and controlled degree of fragmentation.

3) Higher sensitivity is provided, in comparison with PB-MS, since the desolvation chamber sample losses are avoided, and the EI ion source emission current can be much higher since the SMB sample molecules are not scattered from the heated ion source surfaces and thus the ion source temperature does not require stabilization or control and can be very high and non uniform. Furthermore, higher sensitivity is obtained when the sample compounds are monitored through their enhanced molecular ion or in MS-MS experiments on the molecular ion. Monitoring sample compounds via their molecular ion is also highly advantageous since mass spectral matrix interference is exponentially reduced with mass and thus lower chemical noise is encountered with EI of SMB compounds in view of its feature of enhanced molecular ion. In addition, very high sensitivity is enabled with HSI for drugs and PAHs.

4) Linear and uniform response is observed for a broad range of compounds, including non-polar compounds, due to the uniform ionization efficiency of EI, and the high, uniform vaporization of the SMB interface. Thus, semi-quantitative measurements are enabled, without compound-specific calibration procedures. Furthermore, the uniform EI response and nozzle vaporization enable easier MS operation and optimization.

5) A broader range of compounds is amenable for analysis, in comparison with PB-MS, since intra-nozzle thermal vaporization is considerably softer than vaporization inside the heated metal based EI ion source in PB-MS.

6) The problem of peak tailing is smaller than with PB-LC-MS, due to shorter residence time in the heated nozzle and the ability to separately control the nozzle temperature without affecting the obtained mass spectra. Intra EI ion source peak tailing is eliminated for compounds in the SMB due to their free axial passage in the fly through EI ion source.

7) Both very effective GC-MS and LC-MS or liquid sampling MS are enabled in the same apparatus, with minimal or no hardware change.

8) The method of the present invention is also compatible with buffer and salt solution operation, if volatile salts are used, an important advantage in comparison with ES, which is limited in this respect.

9) MS-MS information can be provided with a single mass analyzer.

10) Less matrix effects are expected, due to the complete vaporization of the solvent, sample and matrix.

These features and benefits combined are anticipated to create a new approach for LC-MS that can significantly contribute to improved analysis of samples in liquids. It is noted that in order to obtain these benefits the apparatus must be modified in comparison with particle beam systems that are the present alternative for obtaining LC-MS with electron ionization. The following are the three main modifications.

1. Full sample vaporization must be achieved prior to the expansion into the vacuum system, in contrast to the particle beam method so that a molecular beam of vaporized sample molecules will be formed and not of large particles.

2. The free jet formed after the supersonic expansion must be properly skimmed and collimated at relatively low pressures, in contrast to the situation found in particle beam systems. This requirement is essential in order to prevent shock wave induced heating of the vibrationally cold molecules in the SMB. It is also highly desirable in order to suppress sample losses due to shock wave induced scattering that is far less effective for the much heavier particles in particle beams. Unfortunately, this requirement is translated into greater demand from the vacuum system in comparison with the particle beam method but the resulting advantageous described above justify it.

3. A unique fly through electron ionization ion source is advantageously required for the proper exposition of EI mass spectra of vibrationally cold molecules. The structure of this ion source is very different from that of the standard Nier type EI ion sources currently used in GC-MS and PB-LC-MS systems, and it is similar to Brink type EI ion sources typically used in molecular beam experiments.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF PREFERRED EMBODIMENTS

Figure 1:
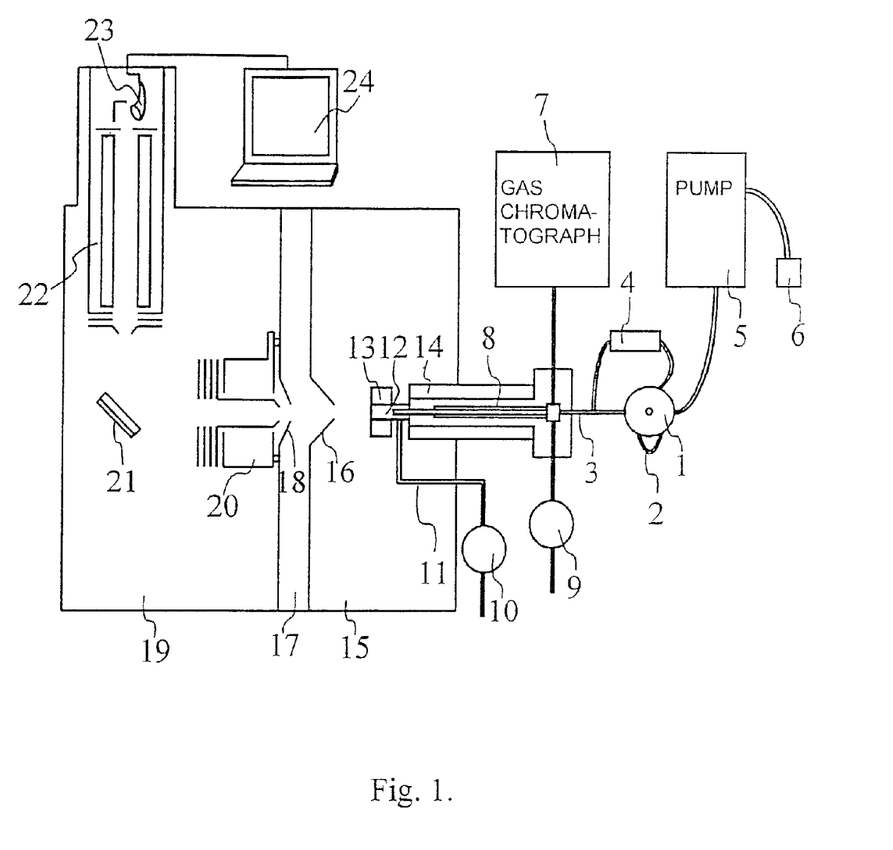
FIG. 1 is a schematic diagram of a mass spectrometric apparatus according to the present invention.

Shown in FIG. 1 is a schematic diagram of a mass spectrometric apparatus according to the present invention, based on supersonic molecular beams and aimed at the analysis of thermally labile sample compounds in solutions. The sample is introduced into the injection system; it can be injected from an injection loop directly to the liquid transfer line, or through a liquid chromatography (LC) column for the separation of the sample compounds in time. The liquid is pumped through the injection system 1, LC column 4 and transfer line 3 by an LC pump 5, which pumps one or a few solvents from the solvent containers 6. The same mass spectrometer apparatus can also accept samples for analysis from a gas chromatograph 7, whose gas flows around or along the liquid sample transfer line 3 in a gas tube 8 that can be coaxial with the liquid transfer line 3. A nebulizing gas, typically helium or hydrogen, is provided via a flow control valve 9 and flows in the coaxial gas tube 8. A further make-up gas, again helium or hydrogen, is provided, and its flow is controlled by valve 10 through make-up gas tube 11. Make-up gas flow tube 11 can also serve as an exit for excess flow rate of the main nebulizing gas, or as a liquid drain for large droplets produced at the spray formation and supersonic nozzle system 12, which is separately heated by heater 13. Liquid transfer line 3 is also separately heated, by heater 14.

The gas mixture of vaporized solvent, sample compounds, and carrier and nebulizing gas expands through the supersonic nozzle into the first vacuum chamber 15 and is skimmed by a skimmer 16. It is then differentially pumped into a second, differential pumping chamber 17, is collimated by the beam collimator 18, and forms a supersonic molecular beam in the third mass analyzer vacuum chamber 19. The SMB sample compounds can be ionized in the "fly-through" EI ion source 20. The structure of this ion source is different from that of standard Nier Type EI ion sources that serve in particle beam instrumentation. It has an open structure with free, unperturbed molecular beam axial passage and meshed ion cage with a long nearby electron emitting filament for increased sensitivity, which also result in high and uncontrolled ion source temperature. The ions are deflected 90° through the ion deflector 21 and analyzed by a standard quadrupole mass analyzer 22. Alternatively, the EI ion deflector 21 is moved downward and a suitable surface is introduced for the HSI of hyperthermal molecules in the SMB. These two ion sources can be combined through the scattering of EI-produced ions on the HSI surface, as will be explained hereinafter. If for certain applications the HSI ion source is not used the structure can be simplified into a coaxial or almost coaxial arrangement of the mass analyzer and the supersonic molecular beam. The mass analyzed ions are detected by the ion detector 23 and the data is processed for sample compound identification and quantification by a computer 24.

Figure 2:
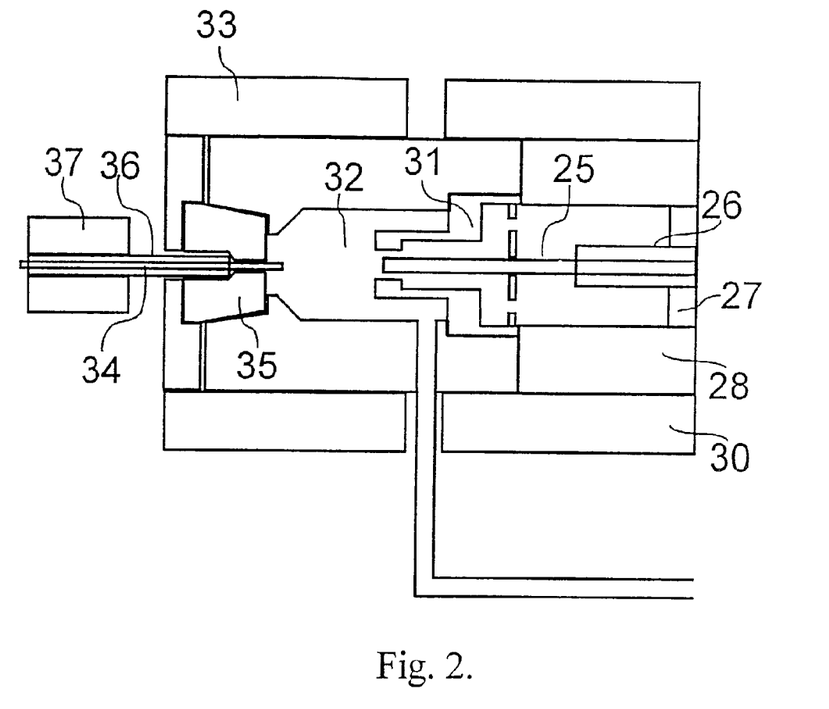
FIG. 2 is a schematic diagram of a further embodiment of the apparatus of FIG. 1.

The present invention is based on vaporization of undissociated, thermally labile compounds. This soft vaporization utilizes very fast thermal vaporization, followed by rapid transfer of the compounds into a supersonic free jet for their ultra-fast vibrational cooling in a supersonic molecular beam. As seen in FIG. 2, the liquid sample is introduced in a tube 25, which can be constituted by a capillary column tube, surrounded by a coaxial flowing gas conduit 26 sealed by a sealing ferrule 27 to the main structure of the soft vaporization unit 28. The temperature of the liquid transfer tube 25 is controlled by heating element 30. A spray is formed in a conventional way, with helium or hydrogen-assisted spray of the liquid eluting from the output of the tube 25 at a controlled temperature. A spray formation nebulizer element 31 serves for the effective production of a thermally assisted, pneumatically controlled, fine spray. The spray formation and desolvation chamber 32 is separately heated and temperature-controlled by a heater 33. The controlled temperature is highly desirable for the thermally assisted nebulization and fine spray formation, and it also serves for the initial droplet and spray desolvation and partial vaporization. The LC column output or sample solution in the tube 25 can be placed inside a coaxial gas conduit 26 that serves for the transfer of the helium or hydrogen nebulizing gas, which is also needed for cooling in the supersonic expansion. The liquid transfer tube 25 ends a short distance before the supersonic nozzle 34, inside the spray formation and desolvation chamber 32. The spray which is formed from the sample solvent and the hydrogen or helium gas, is further dried in this small volume desolvation chamber and enters the supersonic nozzle 34, which is sealed by a nozzle sealing ferrule 35. The supersonic nozzle 34 is preferably made from a 20-mm. long, deactivated capillary column, with an interior diameter of 0.2 mm. This capillary nozzle is carefully separately heated and temperature-controlled over a short portion of its length, using the ceramic tube support 36 and a separate nozzle heater element 37. The nozzle volume is $10^{-4}$ ml. Since sonic carrier gas velocity prevails inside the capillary nozzle, the sample residence time inside the heated nozzle is estimated to be about 10 microseconds or less (10 microseconds per cm carrier gas velocity, or a little more with a high solvent flow rate). The nozzle temperature is adjusted so that during the several microseconds of nozzle passage, the sprayed small droplets are evaporated and the emerging particles are further fully thermally vaporized.

The major idea behind this novel approach is that during the solvent vaporization stage, the compounds are thermally protected by the latent heat of vaporization, which keeps the analyzed compounds relatively cool. Later on, during the short period of heating, due to the relative ineffective energy transfer of helium atoms, vibrational thermal equilibrium is not achieved and the intra-molecular vibrational energy content is limited. The estimated number of gas phase collisions of the carrier gas atoms (and solvent molecules) and sample molecules is about $10^4$-$10^5$. This number seems insufficient to establish a thermal equilibrium with the nozzle wall temperature, as a typical drug compound, with molecular weight of 500, has over 200 vibrational degrees of freedom. In addition, the largely reduced time spent by the compound at the heated nozzle prior to the expansion cooling also provides a substantial further reduction of the degree of dissociation, due to the reduced time available for intra-molecular vibrational energy redistribution that leads to dissociation (simple kinetics considerations). Certainly, this thermal vaporization method is much softer than that of particle beam LC-MS inside the EI ion source, due to the minimal contact with the nozzle surface, much shorter residence time, and lack of thermal equilibrium.

It is estimated that adsorption on the nozzle walls is negligible and that the vaporization is of particles or microdroplets in the gas phase. This estimation is based on the known figure of up to 80 theoretical plates for a GC column 20 mm long and having an internal diameter of 200 μm at about 25 cm/sec carrier gas velocity. At the actual carrier gas velocity of $10^5$ cm/sec in the nozzle, the number of GC theoretical plates will be 0.02, with the implication of about 2% probability of adsorption on the walls. Thus, most of the molecules or particles are swept in a laminar, unperturbed way, without any wall adsorption. In addition, even if a droplet touches a hot surface, the solvent vaporization will form a repulsive pressure as in a GC injector, which pressure will prevent adsorption. As soon as the molecules expand in the SMB, they are vibrationally supercooled and any further dissociation is completely avoided.

Figure 3:
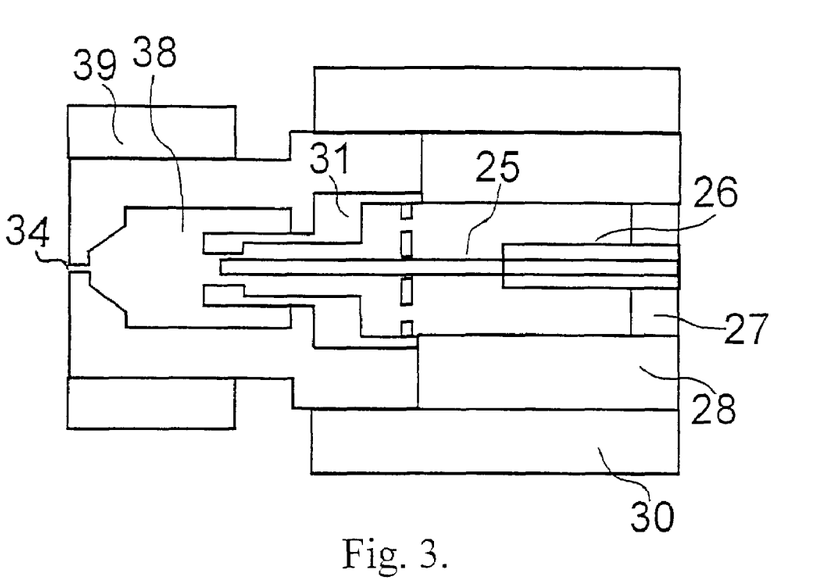
FIG. 3 illustrates a modification of the embodiment of the apparatus of FIG. 2.

In FIG. 3, there is shown a schematic diagram of a slightly modified apparatus for achieving a fast, soft thermal vaporization. Elements 25 to 31 are the same as in FIG. 2. The major difference in this embodiment is that the spray formation, desolvation, vaporization and supersonic nozzle elements are contained in a single chamber 38 which is heated by heater element 39. With this simplified structure, the volume of the spray formation, vaporization and desolvation chamber 38 is reduced, to minimize the time spent by the vaporized sample compounds in the gas phase before their supersonic expansion and subsequent internal vibrational cooling.

Figure 4:
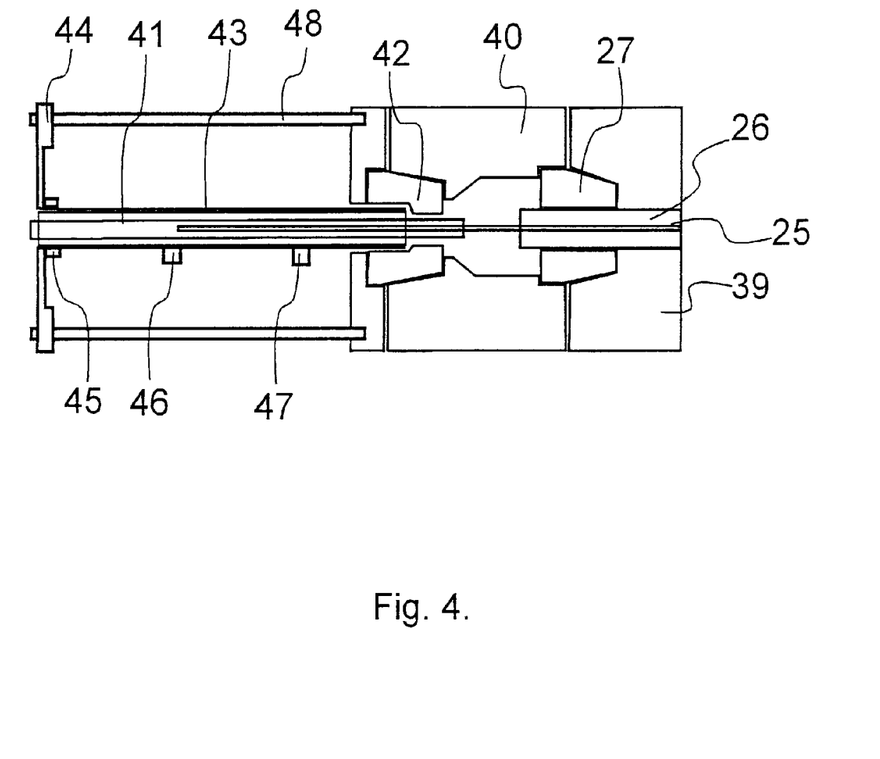
FIG. 4 illustrates a simplified version of the embodiment of the apparatus of FIG. 3.

In FIG. 4, there is shown a schematic diagram of the fast, soft thermal vaporization and desolvation chamber and supersonic nozzle 41 in a form of a capillary tube, that illustrates a simple practical version of the apparatus of FIG. 3. The liquid sample is introduced in a fused silica tube 25, having an internal diameter (ID) of 75 microns and an outside diameter (OD) of 150 microns. The liquid transfer tube 25 is surrounded by a coaxial flowing gas conduit 26, sealed by a sealing ferrule 27 between the back structure 39 and middle chamber structure 40. The liquid transfer tube 25 enters a supersonic nozzle 41 sealed by ferrule 42 to chamber 40. The nozzle 41 is made of standard deactivated fused silica capillary with 0.32 mm ID and 0.45 mm OD, coated with a high temperature Vespel protective coating. The supersonic nozzle capillary tube 40 is placed inside a stainless steel tube 43, that serves as the heater for the spray formation, sample vaporization and supersonic nozzle. Heating tube 43 has 0.53 mm ID and 0.75 mm OD and thus, due to its high electrical resistance, it can be heated by direct current heating. The heating tube 43 is supported on one side by the electrical insulating ferrule 42 and on the supersonic nozzle side by clamp 44, having an electrical contact 45, usually grounded. The nozzle front length can be heated through passing current between contacts 45 and 46 while the spray formation and early vaporization can be enhanced through separate heating by passing current between electrical contacts 46 and 47. A simpler arrangement of only one heating power supply connected to contacts 45 and 47 can also be employed. The supersonic nozzle is positioned and supported by rods 48.

This relatively simple spray formation, sample vaporization and supersonic nozzle structure was found to be effective and useful in the soft thermal vaporization of thermally labile compounds. In addition, the thin, electrically heated tube oven has the advantage of having low thermal conductivity and thus it is characterized by having a large temperature gradient along its length to the unheated chamber 40. This feature was found to be important in preventing too early solvent vaporization, which can cause sample condensation on relatively cool surfaces and eventual clogging of the sample and solvent tube 25. The low thermal mass of this heating system also results in fast thermal equilibration that could be changed or programmed according to experimental needs. In the setup shown in FIG. 4, the sample tube was heated by direct current heating through contacts 46 and 47. This heating induces solvent partial or complete vaporization already inside the sample and solvent tube 25 at its end side and thus its output is of sample particles and/or vaporized molecules. Helium gas is provided and mixed with the output of solvent and sample tube 25, serving as the supersonic expansion gas. This gas is also desirable for serving to improve the heat transfer from the heating tube 43 to the solvent and sample tube 25, as well as for better heat transfer for sample molecule vaporization inside the supersonic nozzle 41. The supersonic nozzle is the 0.32 mm ID column extending past the end of tube 25. Tube 25 can be separately heated through the electrical contacts 45 and 46; however, the heated mixed gas and vaporized solvent also contribute to its temperature. The actual temperature is either measured by a separate thermocouple (not shown) mounted on contact 46 or estimated from the electrical conductivity of the stainless steel tube 43. Typical lengths of the heating tube are 15 mm for each heated thermal zone, separated 10 mm from chamber 40 for thermal insulation. The solvent flow rate in experiments carried out was in the range of 10-200 microliters per minute.

Figure 5:
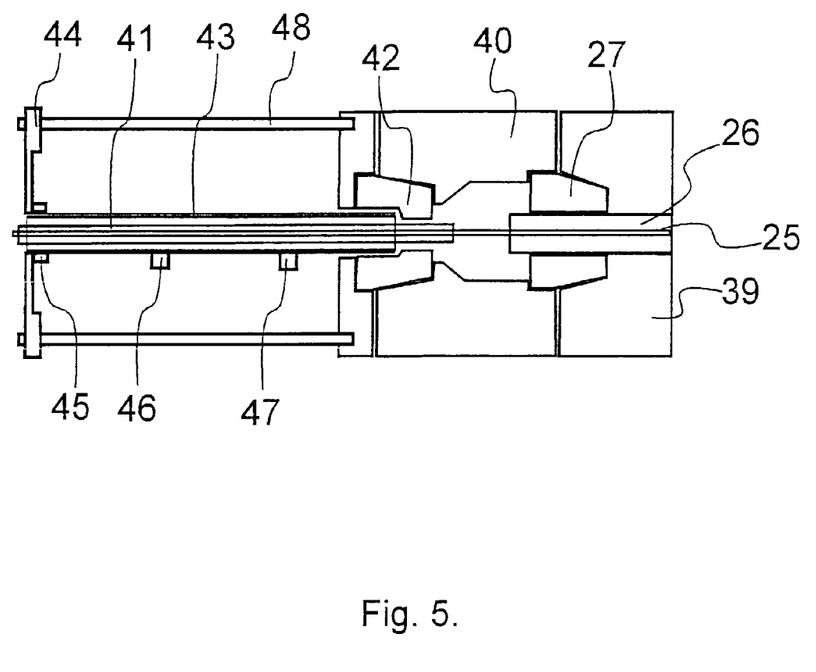
FIG. 5 illustrates a variation in the column position in the embodiment of FIG. 4.

In FIG. 5, there is shown a schematic diagram of the soft thermal vaporization chamber and supersonic nozzle that illustrates a simple variation of the apparatus of FIG. 4. The only change in comparison with FIG. 4 is that the solvent and sample delivery tube 25 now ends slightly, i.e. 1 mm, outside the nozzle tube 41. According to this modification, the sample and solvent delivery tube 25 also serves as the supersonic nozzle and the vaporized solvent molecules, such as methanol, water, acetonitrile or the like, serve as the supersonic expansion gas.

The version of the apparatus illustrated in FIG. 5 works well and is characterized by the following several unique features, in comparison with the apparatus illustrated and described with reference to FIG. 4:

1) No helium or hydrogen gas is needed and thus the gas load on the vacuum pumps is significantly reduced. A relatively simple cryogenic pump can also be used.
2) Since the internal diameter of the solvent and sample tube is much smaller than that of the regular nozzle, cluster formation can appear, depending on the temperature of the heating tube. The temperature range that provides useful mass spectral information is narrower than that of the apparatus shown in FIG. 4. Gas free thermally assisted spray formation can be performed from the delivery tube 25 into a small chamber with a bigger nozzle in order to reduce cluster formation (as in FIG. 4).
3) The clusters formed by the sample and solvent molecules provide additional mass spectral information in the observation of protonated molecular ions, as well as ions of the sample molecule plus one or more solvent molecules. If, however, the heating tube temperature is too low, the signal intensity is significantly reduced due to this clustering.
4) The embodiment of FIG. 5 is estimated to be a little more delicate in handling thermally labile compounds.

It is noted that according to both embodiments of FIGS. 4 and 5, the same apparatus can be used and switching between these two modes of operation can simply be performed by the repositioning of the solvent and sample delivery tube. This repositioning is performed without opening the vacuum system.

The apparatus of FIG. 1 was experimentally tested and several thermally labile compounds that are not amenable for gas chromatography analysis were successfully analyzed. Based on results obtained, it is estimated that the embodiments of FIGS. 4 and 5 are the most useful. The compounds studied include amino acids such as proline and tryptophan, underivatized steroids such as estradiole, stanozolol, cortisone and corticosterone, a vitamin such as β-carotene and antibiotic drugs such as cytidine, spectinomycene, sulphamerazine and reserpine. High quality, library-searchable, EI mass spectra were obtained for all these compounds and no peak tailing was observed.

Figure 6:
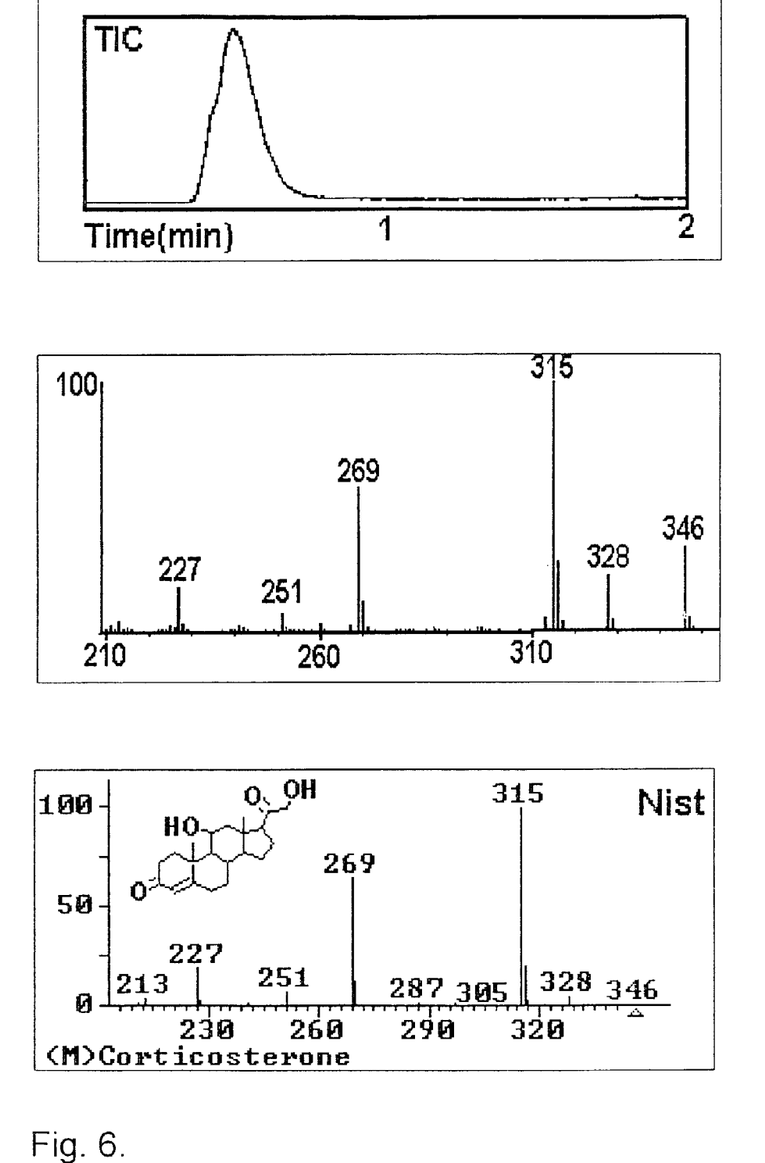
FIG. 6 depicts a typical mass spectrum of corticosterone in methanol solution obtained with an apparatus according to the present invention and its comparison with the standard EI library mass spectrum, as well as the total ion time dependence.

In FIG. 6 a typical EI mass spectrum of corticosterone in methanol solution is shown in the middle plot, obtained with an apparatus according to the present invention, compared with the standard EI library mass spectrum shown in the lower mass spectrum plot. The total ion time dependence is also shown in the upper plot, and it is without tailing. Note the similarity of the library mass spectrum to that obtained by the apparatus according to the present invention. All the ions of m/z 213, 227, 251, 269 and 315 have practically identical relative intensity and thus a good library search is enabled. In addition, the molecular ion at m/z 346 is now clearly observed, while it is missing in the library. The relative abundance of the high mass ion at m/z 328 is also enhanced. Thus, FIG. 6 demonstrates the usefulness of the novel approach of the present invention, both in the analysis of a thermally labile compound and in the provision of enhanced mass spectral information.

EI ionization is certainly the most popular ionization method, due to its uniform response, high sensitivity, rich and informative library searchable mass spectra, and simple construction. According to the present invention, all these known advantages of EI are adapted for LC-MS with SMB. The present invention shares the benefits of these advantages, together with the elimination of the major disadvantage of lack of a molecular ion peak for a large group of compounds. As described herein above, EI in SMB is characterized by enhanced $M^+$, together with all the fragments. The application of EI to LC-MS with SMB was studied and the effects of cluster formation and degree of particle formation and vaporization in the nozzle were explored. It was found that, due to the high temperature of the nozzle and its relatively low pressure of below 1 atmosphere, combined with the use of low molecular weight carrier gas, the effect of cluster formation is negligible, except when the embodiment of FIG. 5 is used. Partial intra-nozzle dissociation is acceptable, as the observed MS of a mixture of the molecule and its pyrolysis products is still informative, especially if the molecular ion is exhibited.

Positive and negative ion chemical ionization are envisioned in the expanding supersonic jet prior to skimming. After the nozzle expansion, the partial carrier gas and solvent pressure is reduced to the 10-0.01 millibar range, which is ideal for chemical ionization.

HSI is potentially a very sensitive ionization method that depends on the kinetic energy of the molecules. Basically, each 1% methanol in the gas phase contributes 0.32 amu to the average carrier gas molecular weight; thus, 6% methanol in hydrogen will provide roughly the same kinetic energy as helium. 6% methanol in 200 ml/min carrier gas flow rate results from a 20 µL/min liquid flow. It was experimentally found that, with caffeine as the sample compound, a liquid methanol flow rate of 4 µL/min enables very effective caffeine HSI. Above this flow rate, the HSI yield drops down, up to a flow rate of 20 µL/min, where HSI becomes significantly less effective. At a much higher flow rate, HSI basically becomes closer to regular surface ionization. However, for large molecules with low ionization potential even the limited aerodynamic acceleration with pure methanol vapor can be sufficient to induce effective HSI. The surface stability under these conditions was tested and it was found that the on-line oxygen cleaning process is efficient and long-term stability is preserved. Hence, HSI is compatible with both direct liquid injection and packed capillary LC-MS analysis.

One of the many possible utilizations of the present invention is the application of surface-induced dissociation (SID) as an alternative technique to MS-MS. It was found that rhenium oxide can serve as a very effective SID surface. Ions that are produced in the EI ion source are directed to the HSI surface for their SID. Two types of SID can be distinguished:

(a) SID of molecules or small clusters for their further dissociation, in order to obtain MS-MS-like information. In this case, the ion optics lens system of the EI ion source is biased to repel ions with relatively low ion energy, and thus, the molecular ions and other very high mass ions are predominantly transmitted. This MS-MS information is provided with a controlled degree of ion dissociation through the scattered ion energy, with only a single, quadrupole mass analyzer.

(b) For highly thermally labile compounds, a complete particle or droplet evaporation might induce dissociation. Thus, the particle is ionized in its fly through the ion source motion and the particle or large cluster ion is scattered from the surface for its dissociation. During the desolvation stage, the molecule is cooled by the heat of desorption absorbed by the evaporating solvent molecules and thus, even very thermally labile compounds are expected to remain intact during this stage. The ionization probability of a very large cluster is increased, due to the presence of many solvent and or sample molecules that can be ionized and induce intra-cluster chemical ionization and charge transfer to the sample compound, which usually possesses a lower ionization potential than the solvent molecule.

The cluster ions are easily distinguished from molecular ions, as methanol clusters form a regular series of $(M+32n)^+$ ions, where n is the number of methanol molecules in the cluster. This could be clearly observed using the apparatus version shown in FIG. 5. On the other hand, fragments are usually unclustered, as the molecular ion bond energies are generally much stronger than the cluster weak bonds which are the first to be broken.

For several applications in which LC separation is not required, it would still be desirable to supplement a GC-MS with SMB apparatus with a liquid flow injection method for the analysis of thermally labile compounds. The use of a standard LC sample loop without any LC column is an obvious way to achieve this goal. An additional approach comprises the use of an uncoated short microbore column, connected from a GC injector to the nozzle, with the same interface as described above with reference to FIGS. 1-5 for LC-MS. One, or a few, microliter droplets are injected into a cool injector and deactivated, uncoated fused silica capillary. The helium flow pushes the droplet to the nozzle and thus a time-integral, quantitative measurement can be obtained. This method excels in providing a quantitative measurement, while the memory effect due to adsorption on the deactivated fused silica is small. It is noted that for large molecules, the separation power of the MS is increased. This is especially true with EI in SMB, which provides enhanced $M^+$. Thus, the need for the time-consuming LC separation might be reduced and flow injection can be a useful alternative for some applications. This flow injection method extends the range of molecules amenable for MS analysis with GC-MS with SMB instrumentation, at only a negligible additional cost, and thus it seems desirable. In addition, it is a simple way to achieve a fast, automated screening (using the GC auto-sampler) of drugs and other samples in simple mixtures.

An additional benefit of the present invention is the combination of GC-MS and LC-MS instruments in one apparatus. Accordingly, the same transfer line that couples the GC column to the nozzle also serves to transfer the LC liquid transfer column. Both the GC and LC can be connected simultaneously, due to the ability of the nozzle to handle a relatively high gas flow rate. The same nozzle that serves for the liquid sampling mass spectrometry is very effective for GC-MS, and the concentric arrangement of the GC and LC sample transfer lines enables fast GC-MS and LC-MS switching.

As discussed above, the SMB interface is optimized for handling liquid flow rates up to 200 μL/min with EI and up to 20 μL/min flow rate with HSI. Conventional LC operates with 4.6 mm ID columns and 1 ml/min flow rate. Recently, columns having an internal diameter of 2 mm and a 200 μL/min flow rate have become popular, and microbore LC columns having an internal diameter of 1 mm with 50 μL/min optimal column flow rate are finding growing use, especially with LC-MS. This flow rate is fully compatible with the EI LC-MS method described above. LC Packings and other companies have developed and are marketing packed capillary columns having an internal diameter of 0.32 mm and optimal flow rate of 4 μL/min, that seem ideal for this method and apparatus including with HSI. However, for certain applications, it is desirable to enable standard flow rate acceptance. The simplest approach is to split the column effluent before its coupling with the supersonic nozzle, but this method also results in a loss of sensitivity. An alternative method is based on the use of the particle beam desolvation chamber for effective solvent flow removal, combined with enhanced centerline sample compound enrichment prior to the full vaporization nozzle. This process can be aided by a pre-nozzle operated at a higher pressure of a few atmospheres and enrichment expansion to the nozzle area at 1 atmosphere. A solvent permeable membrane can also be used for the selective depletion of solvent molecules and solvent load reduction. On the other hand, for some forms of liquid separation technologies such as capillary electrophoresis, it might be needed to add some make-up liquid for the stabilization of the soft thermal vaporization process.

It will be evident to those skilled in the art that the invention is not limited to the details of the foregoing illustrated embodiments and that the present invention may be embodied in other specific forms without departing from the essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. Mass spectrometric method for analyzing a sample in a liquid solution for producing mass spectral information having an enhanced molecular ion for identifying and/or quantifying the chemical content of the sample, comprising the steps of:

directing a flow of a solution containing sample compounds to be analyzed towards a supersonic nozzle;
   vaporizing the solution containing the sample compounds;
   expanding the vaporized sample from said supersonic nozzle into a vacuum system, forming a supersonic molecular beam;
   ionizing with electrons the vaporized sample compounds;
   mass analyzing the ions formed from said sample compounds;
   detecting said ions formed from said sample compounds after mass analysis;
   processing the data obtained from the resulting mass spectral information for identifying and/or quantifying the chemical content of said sample, and wherein the flow of said solution is a liquid flow;
   said sample compounds vaporization being aided by a prior solvent spray formation;
   said spray droplets are evaporated and the emerging sample particles are further vaporized to form vaporized sample molecules;
   the vaporization of said sprayed directed flow of a solution containing sample compounds is effected prior to its expansion from said supersonic nozzle;
   cooling said vaporized sample compounds through its expansion from said supersonic nozzle;
   forming a supersonic molecular beam of both, vibrationally cold sample compounds and solvent molecules;
   the ionization of said vibrationally cold sample compounds while contained in said supersonic molecular beam in a fly through electron ionization ion source; whereby to produce mass spectra with enhanced molecular ions; and
   said data obtained from the resulting mass spectral information includes enhanced molecular ions compared with the particle beam method for improved identifying and/or quantifying of the chemical content of said sample.

2. The method according to claim 1, wherein said sample is vaporized prior to reaching said supersonic nozzle.

3. The method according to claim 1, wherein said sample vaporization is performed inside said supersonic nozzle.

4. The method according to claim 1, wherein said sample vaporization is aided by a prior solvent nebulization and spray formation before the expansion of said vaporized sample from said supersonic nozzle.

5. The method according to claim 4, wherein said sample solvent is selectively removed prior to its expansion effected by said supersonic nozzle.

6. The method according to claim 1, wherein said solvent and sample are nebulized to form a spray and the spray is vaporized into sample compounds and solvent molecules, inside a heated channel supersonic nozzle.

7. The method according to claim 1, wherein said solution and sample are vaporized using thermally assisted spray formation without added gas.

8. The method according to claim 1, wherein sample identification and quantification is based on standard electron ionization libraries.

9. The method according to claim 1, wherein said sample is directed towards said supersonic nozzle by flow injection.

10. The method according to claim 1, wherein said sample is directed towards said supersonic nozzle from a liquid chromatograph.

11. The method according to claim 10, wherein said ions are ions of large clusters of said sample and solvent.

12. The method according to claim 1, wherein ions formed from said sample are scattered from a suitable surface for surface-induced dissociation.

13. A mass spectrometric apparatus for analyzing a sample in a liquid solution for producing mass spectral information to provide an enhanced molecular ion for improved identifying and/or quantifying the chemical content of the sample, comprising:

means for directing a flow of a solution containing sample compounds to be analyzed towards a supersonic nozzle;

means for thermal vaporization of said solution containing sample compounds;

said supersonic nozzle and vacuum system enabling expansion of said vaporized sample compounds into said vacuum system, forming a supersonic molecular beam;

electron ionization ion source means for ionizing said vaporized sample compounds;

mass analyzer means for the mass analysis of the ions formed from said sample compounds;

an ion detector for detecting said ions formed from said sample compounds after mass analysis; and means for data processing of the mass spectral information obtained for identifying and/or quantifying the chemical content of said sample, wherein said means for directing a flow of a solution includes a tubular liquid transfer line;

said means for thermal vaporization include means for solvent spray formation prior to said sample compounds vaporization followed by its expansion from said supersonic nozzle;

said supersonic nozzle expands said vaporized sample compounds with subsequent internal vibrational cooling;

said supersonic molecular beam contains both vaporized solvent and vibrationally cold sample compounds;

said electron ionization ion source means is located downstream of said supersonic nozzle and is a fly through ion source for the ionization of said sample compounds while contained in said supersonic molecular beam as vibrationally cold compounds;

said supersonic nozzle, vacuum system and fly through ion source provide enhanced molecular ions in the mass spectra of vibrationally cold compounds; and said means for data processing of the mass spectral information obtained is adopted for improved identifying and/or quantifying the chemical content of said sample by the availability of enhanced molecular ions compared with the particle beam method.

14. The apparatus according to claim 13, further comprising means for solvent nebulization and spray formation before the expansion of said vaporized sample from said supersonic nozzle.

15. The apparatus according to claim 14, wherein said means for solvent nebulization and spray formation is based on thermally assisted spray formation without added gas.

16. The apparatus according to claim 13, further comprising means for the selective removal of the solvent prior to its expansion effected by said supersonic nozzle.

17. The apparatus according to claim 13, wherein said supersonic nozzle is a pinhole nozzle.

18. The apparatus according to claim 13, wherein said supersonic nozzle is a channel nozzle.

19. The apparatus according to claim 18, wherein said channel supersonic nozzle is heated by means of direct current heating of a heating tube.

20. The apparatus according to claim 13, wherein said means for directing a flow of a solution with the sample to be analyzed towards a supersonic nozzle, is based on flow injection.

21. The apparatus according to claim 13, wherein said means for directing a flow of a solution with the sample to be analyzed towards a supersonic nozzle, is a liquid chromatograph.

22. The apparatus according to claim 13, further including means for scattering ions formed from said sample from a suitable surface, for surface-induced dissociation.

23. A mass spectrometric method for analyzing a sample in a solution for identifying and/or quantifying the chemical content of a sample, comprising the steps of:

directing a flow of a solution containing sample compounds to be analyzed towards a supersonic nozzle;

vaporizing the solution containing the sample compounds;

expanding the vaporized sample from said supersonic nozzle into a vacuum system, forming a supersonic molecular beam;

ionizing with electrons the vaporized sample compounds;

mass analyzing the ions formed from said sample compounds;

detecting said ions formed from said sample compounds after mass analysis;

processing the data obtained from the resulting mass spectral information, for identifying and/or quantifying the chemical content of said sample, and wherein the flow of said solution is a liquid flow;

said sample compounds vaporization being aided by a prior solvent spray formation;

said spray droplets are evaporated and the emerging sample particles are further vaporized to form vaporized sample molecules;

the vaporization of said sprayed directed flow of a solution containing sample compounds is effected prior to its expansion from said supersonic nozzle;

cooling said vaporized sample compounds through its expansion from said supersonic nozzle;

forming a supersonic molecular beam of both, vibrationally cold sample compounds and solvent molecules, and the ionization of said vibrationally cold sample compounds while contained in said supersonic molecular beam in a fly through electron ionization ion source.

24. A mass spectrometer apparatus for analyzing a sample in a solution for identifying and/or quantifying the chemical content of a sample, comprising:

means for directing a flow of a solution containing sample compounds to be analyzed towards a supersonic nozzle;

means for vaporizing said solution containing sample compounds;

said supersonic nozzle enabling expansion of said vaporized sample compounds into a vacuum system, forming a supersonic molecular beam;

electron ionization ion source means for ionizing said vaporized sample compounds;

mass analyzer means for the mass analysis of the ions formed from said sample compounds;

an ion detector for detecting said ions formed from said sample compounds after mass analysis, and means for data processing of the mass spectral information obtained for identifying and/or quantifying the chemical content of said sample, wherein said means for directing a flow of a solution includes a tubular liquid transfer line;

means for solvent spray formation prior to said sample compounds vaporization;

thermal vaporization means for vaporizing said directed flow of solution and sample compounds from its spray droplets prior to its expansion from said supersonic nozzle;

said supersonic nozzle expands said vaporized sample compounds with subsequent internal vibrational cooling;

said supersonic nozzle and vacuum system form a supersonic molecular beam of both vaporized solvent and vibrationally cold sample compounds, and said electron ionization ion source means is located downstream of said supersonic nozzle and is a fly through ion source for the ionization of said sample compounds while contained in said supersonic molecular beam as vibrationally cold compounds.

* * * * *